United States Patent [19]
Koeneman

[11] 4,292,694
[45] Oct. 6, 1981

[54] PROSTHESIS ANCHORING MEANS

[75] Inventor: James B. Koeneman, Erie, Pa.

[73] Assignee: Lord Corporation, Erie, Pa.

[21] Appl. No.: 162,714

[22] Filed: Jun. 25, 1980

[51] Int. Cl.³ .............................................. A61F 1/24
[52] U.S. Cl. ....................................... 3/1.91; 3/1.911; 3/1.912; 128/92 C
[58] Field of Search ................................. 3/1.9–1.913; 128/92 C, 92 CA; 433/173, 201

[56] References Cited

U.S. PATENT DOCUMENTS

| | | | |
|---|---|---|---|
| 3,605,123 | 9/1971 | Hahn | 3/1.9 |
| 3,707,006 | 12/1972 | Borkros et al. | 3/1.9 |
| 3,855,638 | 12/1974 | Pilliar | 128/92 C X |
| 3,938,198 | 2/1976 | Kahn et al. | 3/1.192 |
| 3,971,134 | 7/1976 | Bokros | 128/92 C X |
| 3,986,212 | 10/1976 | Sauer | 3/1.91 |
| 4,038,703 | 8/1977 | Bokros | 3/1.91 X |
| 4,051,598 | 10/1977 | Sneer | 128/92 C X |
| 4,164,794 | 8/1979 | Spector et al. | 3/1.91 X |
| 4,231,120 | 11/1980 | Day | 3/1.91 |

FOREIGN PATENT DOCUMENTS 2247721 4/1974 Fed. Rep. of Germany ....... 3/1.912
2444831 9/1975 Fed. Rep. of Germany ......... 3/1.91

Primary Examiner—Ronald L. Frinks
Attorney, Agent, or Firm—Thomas L. Kautz

[57] ABSTRACT

A means of anchoring the stem or other portion of a joint prosthesis inserted within the medullary canal of a bone adjacent a diseased or damaged joint is provided by the present invention, wherein a continuous jacket or a plurality of circumferential rings of elastomeric material are attached to the prosthesis stem. A series of arrays of at least three section of biocompatible rigid material are secured to the elastomeric material at selected intervals along the length of the stem and extend radially outwardly therefrom, such that upon insertion of the prosthesis stem within the medullary canal the elastomeric material is compressed and urges the rigid sections outwardly into secure contact with the adjacent bone to resist dislocation of the prosthesis within the medullary canal.

8 Claims, 3 Drawing Figures

PROSTHESIS ANCHORING MEANS

FIELD OF THE INVENTION

The present invention relates generally to the field of prostheses, and, more specifically, to a means for anchoring the stem portion of a joint prosthesis within the medullary canal of the bone adjacent a diseased or damaged skeletal joint to provide stability, particularly during the initial bone ingrowth state of post-operative rehabilitation.

BACKGROUND OF THE INVENTION

In recent years, prosthetic devices have been developed and are now in widespread use as attachments, reinforcements or replacements of various members and joints of the human skeletal system. Many modern joint prostheses, including those for replacement of the hip, finger, wrist, elbow and various other joints, are shaped for insertion into the medullary canal of the adjacent bone to secure the prosthesis in place. Synthetic bone cement is one widely used method of securing such prostheses in position within the medullary canal, but it has recently been discovered that problems with this technique include incomplete filling of the cavity of the bone, toxicity of the cement and possible necrosis of the adjacent layer of cancellous or cortical bone. Although bone cement is relatively easy to use in surgical procedures, the above-named problems have prompted development of alternate means of securing prostheses within the medullary canal of the bone adjacent the diseased or damaged joint.

As is well known, bone ingrowth may be accepted by protheses formed of materials having a surface porosity of at least 45 microns. Clinical studies have confirmed that bone ingrowth not only avoids the problems of bone cement, but actually provides better stability of the prosthesis over an extended period of time and may result in improved stress distribution between the prosthesis and adjacent bone. Various prior art patents including U.S. Pat. No. 3,707,006 to Bokros et al and U.S. Pat. No. 3,938,198 to Kahn et al, have recognized the advantage of securing the prosthesis within the medullary canal through bone ingrowth rather than bone cement. As discussed in Bokros et al and Kahn et al, several materials have been utilized to promote bone ingrowth, including porous ceramic coated with pyrolitic carbon, surface treated titanium, cobalt-chrome and stainless steel alloys and various fibrous overlayers such as polysulfone, Teflon ® coated graphite fiber and polyethylene terephthalate woven mesh.

A major limitation of existing prostheses utilizing bone ingrowth rather than bone cement, is that no fastening or securing means are provided to anchor the stem portion of the prosthesis along its entire length within the medullary canal. The Kahn et al patent, for example, discloses a hip joint prosthesis in which the flange of the femoral head prostehsis is pinned to the cortical bone of the femur, but the stem portion is free to move within the medullary canal of the femur. Recent clinical studies have indicated that movement or shifting of the prosthesis within the medullary canal during the initial four to six weeks of postoperative rehabilitation can interrupt or prohibit bone ingrowth thus delaying or severly hampering patient recovery. It can be appreciated that the alternative of keeping a patient essentially immobilized for that period of time to avoid such movement of the prosthesis is very difficult.

SUMMARY OF THE INVENTION

The present invention avoids the problems of stability encountered with existing methods of securing prostheses in place to permit bone ingrowth, by providing means to anchor the entire length of the stem or other segment of the prosthesis which is inserted into the medullary canal of the bone adjacent a damaged or diseased joint. In one embodiment of the subject invention, a plurality of circumferential elastomeric rings are disposed at spaced intervals along the length of the stem portion of the prosthesis. Attached at spaced intervals to each of the circumferential rings are a plurality of spacers, formed of porous titanium or a suitable equivalent, which contact the walls of the medullary canal. The circumferential elastomeric rings and spacers are sized such that the combined diameter of the stem portion of the prosthesis is slightly larger than the diameter of the medullary canal. Upon insertion of the stem portion into position, the elastomeric rings are compressed and thus urge the spacers against the walls of the medullary canal holding the prothesis securely in place, and resisting dislocation which could be caused by movement of the patient.

In an alternate embodiment of the subject invention, a continuous jacket of elastomeric material is attached to the stem or other segment of the prosthesis inserted within the medullary canal of the bone adjacent the joint to be replaced. Spacers, formed of porous titanium or an equivalent, are disposed at intervals about the circumference of the elastomer jacket and stem, and a series of such circumferential spacers attached at spaced intervals along the length of the stem.

It is therefore an object of the present invention to provide a means of anchoring the stem portion of a prosthesis which is inserted into the medullary canal of the bone adjacent a damaged or diseased joint.

It is another object of the present invention to affix a series of circumferential elastomeric rings at spaced intervals along a prosthesis stem formed for insertion within the medullary canal of bone, each ring having a plurality of titanium sections attached thereto which extend outwardly into contact with the walls of the medullary canal. The total diameter of the prosthesis stem, elastomeric rings and titanium is greater than that of the medullary canal such that the elastomer is compressed upon insertion therewithin forcing the titanium sections into secure engagement with the medullary canal for holding the prosthesis in place during the initial stages of post-operative bone ingrowth.

DESCRIPTION OF THE DRAWINGS

Objects in addition to the foregoing will become apparent upon consideration of the following description taken in conjunction with the drawings wherein.

DETAILED DESCRIPTION OF THE INVENTION

Figure 1:
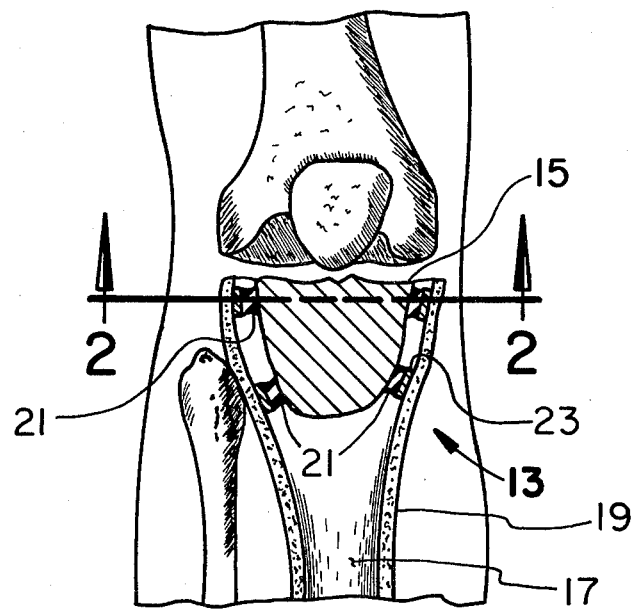
FIG. 1 is a partial cross-sectional view of one embodiment of the present invention shown in combination with a tibial plateau prosthesis.
Figure 2:
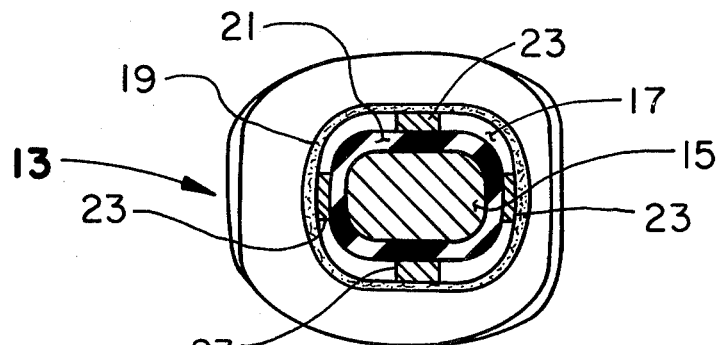
FIG. 2 is a cross-sectional view of the embodiment of FIG. 1 taken generally along line 2—2 of FIG. 1.

Referring now to FIGS. 1 and 2, one embodiment of the securing means of the subject invention labelled generally with the reference 13, is shown supporting a tibial plateau prosthesis 15 within the medullary canal 17 of the tibia 19. It should be understood that the securing means shown herein may be utilized with a variety of other joint prostheses including those for replacement of the hip, wrist, elbow and ankle, and the tibial plateau prosthesis 15 is used herein only for purposes of discussion and illustration. The prosthesis securing means 13 includes a plurality of circumferential elastomeric rings 21 attached at spaced intervals along the length of tibial plateau prosthesis 15. Spacers 23, formed of a rigid biocompatible material, are attached at spaced intervals about the elastomeric rings 23 and extend radially outwardly. Four spacers 23 are shown in this embodiment, but it should be understood that as few as three spacers 23 may be used and more than four spacers 23 would also be acceptable. The elastomeric rings may be bonded to the spacers 23 by vulcanization, adhesive coatings or any other suitable means. Spacers 23 are formed of titanium, cobalt-chrome, stainless steel or a polymeric material, and are preferably treated in a known manner to produce a surface porosity of at least 45 microns for acceptance of bone and tissue ingrowth.

The combined diameter of the tibial plateau prosthesis 15, elastomeric rings 21 and spacers 23 is greater than that of the medullary canal 17 of the tibia 19. Thus, upon insertion of the prosthesis 15 into the medullary canal 17, the elastomeric rings 23 are compressed and urge spacers 23 into contact with the tibia 19 along the entire length of the prosthesis 15.

Figure 3:
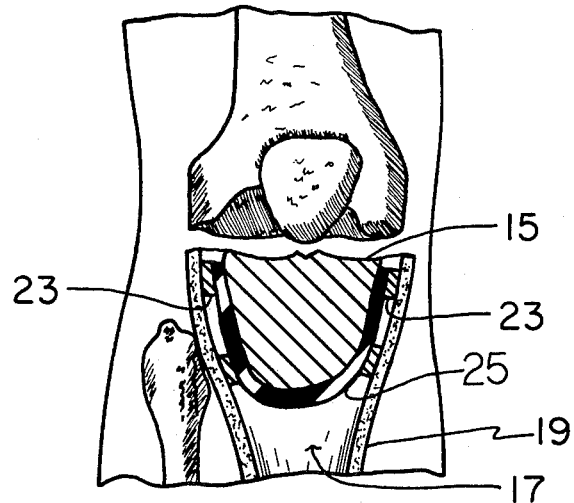
FIG. 3 is a partial cross-sectional view of an alternate embodiment of the prosthesis shown in FIG. 1.

Referring now to FIG. 3, an alternate embodiment of the securing means herein is shown. In this embodiment, a continuous layer or jacket 25 of elastomeric material is attached to the outer surface of the tibial plateau prosthesis 15. Three or more spacers 23, forming an array, are attached at spaced intervals about the circumference of elastomeric jacket 25 in a plane perpendicular to the longitudinal axis of prosthesis 15. A series of such arrays of spacers 23 are disposed at selected locations along the length of prosthesis 15, and extend outwardly into contact with the walls of the medullary canal 17. The combined diameter of the tibial plateau prosthesis 15, elastomeric jacket 25 and spacers 23 is greater than that of the medullary canal 17 of tibia 19, such that upon insertion of prosthesis 15 within the medullary canal 17 the elastomeric jacket 25 is compressed and urges spacers 23 outwardly into secure contact with the tibia 19. Thus, anchoring of prosthesis 15 is accomplished in a manner similar to that in the embodiment of FIG. 1.

The anchoring means of the present invention resist dislocation of a joint prosthesis by providing secure engagement between the stem portion of the prosthesis and the medullary canal of the bone adjacent the diseased or damaged joint. The stem or other segment of the prostheses inserted within the medullary canal (e.g. tibial plateau) are held along their entire length, unlike prior art prostheses which are typically pinned or secured by bone screws at a single location. The stability provided to joint prostheses by the present invention greatly reduces the chances of obtaining inadequate or improper bone and tissue ingrowth during the critical initial stages of postoperative rehabilitation, and thus enhances and accelerates patient recovery from the surgical procedure.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A securing means for anchoring the stem portion of a joint prosthesis inserted within the medullary canal of the bone adjacent a damaged or diseased skeletal joint, comprising a plurality of resilient elastomeric rings disposed about the circumference of said stem portion at spaced intervals along the length thereof, and a plurality of sections of rigid material attaching at spaced intervals about each of said elastomeric rings and extending radially outwardly therefrom, the combined diameter of said stem portion, said elastomeric rings and said sections of rigid material being greater than the diameter of said medullary canal, said elastomeric rings being compressed upon insertion of said stem portion into said medullary canal and thereby urging said sections of rigid material into contact with said bone for resisting dislocation of said prosthesis within said medullary canal.

2. The securing means of claim 1 wherein said sections of rigid material are formed from material selected from the group consisting of titanium, cobalt-chrome, stainless steel, or a biocompatible polymer.

3. The securing means of claim 1 wherein the outer surface of said sections of rigid material is treated to produce a surface porosity of at least 45 microns to accept bone and tissue ingrowth.

4. In a joint prosthesis for replacing a diseased or damaged skeletal joint in the human body, said joint prosthesis having a segment shaped for insertion into the medullary canal of the bone adjacent said skeletal joint, the improvement comprising securing means including a plurality of resilient elastomeric rings disposed about the circumference of said segment at spaced intervals along the length thereof, and a plurality of sections of rigid material attaching at spaced intervals about each of said elastomeric rings and extending radially outwardly therefrom, the combined diameter of said segment, said elastomeric rings and said sections of rigid material being greater than the diameter of said medullary canal, said elastomeric rings being compressed upon insertion of said segment into said medullary canal and thereby urging said sections of rigid material into contact with said bone for resisting dislocation of said prosthesis within said medullary canal.

5. The securing means of claim 4 wherein said sections of rigid material are formed from material selected from the group consisting of titanium, cobalt-chrome, stainless steel, or a biocompatible polymer material.

6. The securing means of claim 4 wherein the outer surface of said sections of rigid material is treated to produce a surface porosity of at least 45 microns to accept bone and tissue ingrowth.

7. A securing means for anchoring the stem portion of a joint prosthesis inserted within the medullary canal of the bone adjacent a diseased or damaged skeletal joint comprising a layer of elastomeric material attaching to the outer surface of said stem portion, and a plurality of sections of rigid material attaching at spaced intervals about said elastomeric layer in a plane generally perpendicular to the longitudinal axis of said stem portion to form an array, a plurality of said arrays of sections of rigid material attaching at selected intervals along the length of said stem portion, the combined diameter of said stem portion, elastomeric layer and sections of rigid material in an array being greater than the diameter of said medullary canal, said elastomeric layer being compressed upon insertion of said stem portion into said medullary canal and thereby urging said sections of rigid material to said arrays into contact with said bone for resisting dislocation of said prosthesis within said medullary canal.

8. In a joint prosthesis for replacing a diseased or damaged skeletal joint in a human body, said joint prosthesis having a segment shaped for insertion into the medullary canal of the bone adjacent said skeletal joint, the improvement comprising securing means including a layer of elastomeric material attaching to the outer surface of said segment, and a plurality of sections of rigid material attaching at spaced intervals about said elastomeric layer in a plane generally perpendicular to the longitudinal axis of said segment to form an array, a plurality of said arrays of sections of rigid material attaching at selected intervals along the length of said segment, the combined diameter of said segment, elastomeric layer and sections of rigid material in an array being greater than the diameter of said medullary canal, said elastomeric layer being compressed upon insertion of said segment into said medullary canal and thereby urging said sections of rigid material in said arrays into contact with said bone for resisting dislocation of said prosthesis within said medullary canal.

* * * * *